United States Patent [19]

Ollar

[11] Patent Number: 5,316,918
[45] Date of Patent: May 31, 1994

[54] METHOD AND APPARATUS FOR TESTING MAI (MYCOBACTERIUM AVIUM-INTRACELLULARE) FOR ANTIMICROBIAL AGENT SENSITIVITY

[75] Inventor: Robert A. Ollar, Milford, Pa.

[73] Assignee: Infectech, Inc., Milford, Pa.

[21] Appl. No.: 841,937

[22] Filed: Feb. 25, 1992

Related U.S. Application Data

[63] Continuation-in-part of Ser. No. 426,573, Oct. 24, 1989, Pat. No. 5,153,119.

[51] Int. Cl.$^5$ .............. C12Q 1/00; C12Q 1/02; C12Q 1/18; C12N 1/20
[52] U.S. Cl. .......................... 435/34; 435/4; 435/29; 435/32; 435/863; 435/864; 435/732; 435/252.1; 435/253.1
[58] Field of Search ............... 435/4, 29, 32, 34, 863, 435/864, 7.32, 7.92, 252.1, 252.3

[56] References Cited

U.S. PATENT DOCUMENTS 3,826,717  7/1974  Gilbert et al. ..................... 435/33

OTHER PUBLICATIONS

Heifets et al Antimicrobial Agents & Chematherapy 1989: 33: 1298–1301.
Ollar et al Tubercle (1990) (23–28).
Wallace, J. M. et al, "*Mycobacterium avium* Complex in Patients with Acquired Immunodeficiency Syndrome—A Clinicopathologic Study", *Chest*, 93(5):926–932 (1988).
Kirihara, J. M. et al., "Improved Detection Times For *Mycobacterium avium* Complex and *Mycobacterium tuberculosis* with BACTEC Radiometric System", *J. Clin. Microbiol.*, 22:841–845 (1985).
Gonzales, R. et al., "Evaluation of Gen-Probe DNA Hybridization Systems for the Identification of *Mycobacterium tuberculosis* and *Mycobacterium avium-intracellulare*", *Diagnosis Microbiology Infect. Dis.*, 8:69–77 (1987).

Fuhs, G. W., "Der Microbielle Abbau Von Kohlenwasserstoffen", *Arch. Microbiol.* 39:374–422 (1961).
Mishra, S. K., et al, "Observations On Paraffin Baiting As a Laboratory Diagnostic Procedure in Nocardiosis", *Mycopathologica and Mycologica Applicata* 51 (2–3): 147–157 (1973).
Ollar, R.-A., "A Paraffin Baiting Technique that Enables a Direct Microscopic view of *in situ* Morphology of *Nocardia asteroides* with the Acid–Fast or Fluorescence Staining Procedures", *Zbl. Bakt. Hyg., Abt. Orig. A*, 234:81–90 (1976).
Singh, M. et al., "Comparison of Paraffin Baiting and Conventional Culture Techniques for Isolation of *Nocardia asteroides* from Sputum", *Journal of Clinical Microbiology*, vol. 25, No. 1, Jan. 1987 pp. 176–177.
Heifets, L. et al., "Comparison of Bacterial Activities Of Streptomycin, Amikacin, Kamamycin and Capreomycin against *Mycobacterium Avium* And *M. Tubervulosis*", *Antimicrob. Ag. Chemother.*, 1989:33:1298–1301.
Inderlied, C. B. et al., "*In vitro* and *in vivo* Activity of Azithromycin (CP 62,993) Against The *Mycobacterium avium* Complex", *J. Infect. Dis.*, 1989:159:994–997.

(List continued on next page.)

Primary Examiner—Michael G. Wityshyn
Assistant Examiner—Jane Williams
Attorney, Agent, or Firm—Arnold B. Silverman; David V. Radack

[57] ABSTRACT

An apparatus and method for determining the sensitivity of MAI to different antimicrobial agents and dosages thereof is provided. The apparatus comprises a plurality of test tubes adapted to contain an amount of an antimicrobial agent to be tested and MAI complex organisms to be assayed and a separate paraffin coated slide adapted for placement in each of the test tubes. The growth of the MAI complex organisms on the slide can be used to determine the concentration of the antimicrobial agent necessary to resist MAI complex organism growth on the slide. An associated method is also disclosed.

7 Claims, 2 Drawing Sheets

OTHER PUBLICATIONS

Inderlied, C. B. et al, "Determination of in vitro susceptibility of *Mycobacterium avium* Comples Isolates To Antimyobacterial Agents By Various Methods", *Antimicrob. Ag. Chemother.*, 1987:32:1697–1702.

O'Hara, C. M. et al, "Enterobacter hormaechei, a New Species of the Family *Enterobacteriaceae* Formerly Known as Enteric Group 75", *J. Clin. Microbiol.*, vol. 27, No. 9, pp. 2046–2049 (1989).

Poropatich, C. O. et al., "Acid–Fast Smear and Culture of Respiratory Secretions, Bone Marrow, and Stools as Predictors of Disseminated *Microbacterium avium* Complex Infection", *J. Clin. Microbiol.*, vol. 25, No. 5, pp. 929–930 (1987).

Warren, N. G. et al., "An Improved Reagent for Mycobacterial Nitrate Reductase Tests", *J. Clin. Microbiol.*, vol. 18, No. 1, pp. 546–549 (1983).

Ollar, R.-A. et al., "The use of paraffin wax metabolism in the speciation of *Mycobacterium avium–intracellulare*", *Tubercle*, 77:23–28 (1990).

Mishra, S. K. et al., "Application of Paraffin Bait Technique to the Isolation of *Nocardia asteroides* from Clinical Specimens", *Applied Microbiol.*, vol. 18, No. 4 (Oct. 1969).

Resnick et al., *Biol. Abstr.*, 86(8):AB–169, Abstract #77742, 1989.

Cox et al., *Biol. Abstr.*, 65(10), Abstract #59630, 1978.

Sohngen, N. L., "Benzin, Petroleum, Paraffinol und Paraffin als Kohlenstoff–und Energieguelle fur Mikroben", *Centralb. F. Bakt., Abt. II Bd.*, 37:595–609 (1913).

Ollar, R.-A. et al., "A modified broth dilution assay for antibiotic sensitivity testing of *Mycobacterium avium–intracellulare* using paraffin slide cultures", *Tubercle*, 73:000–000 (1991).

Gordon, R. E. et al., "The Isolation Of Acid–Fast Bacteria From Soil", *Jour. of Inf. Disease*, vol. 59, pp. 200–206 (1936).

Kurup, P. V. et al., "Use Of Paraffin Bait Technique In The Isolation of *Nocarbia asteroides* From Sputum", *Mycopath. Mycol. Appl.*, vol. 40, pp. 363–367 (1970).

Rosen, I. G., "The Use of DNA Probes for the Diagnosis of Infectious Diseases", *Pharmaceutical Technology*, Sep., 1987.

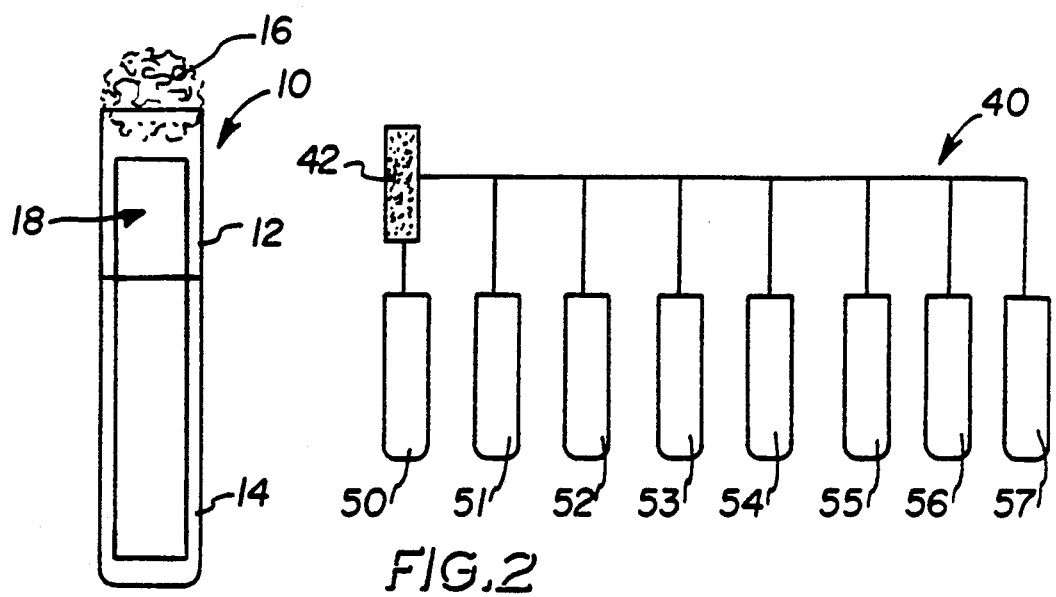
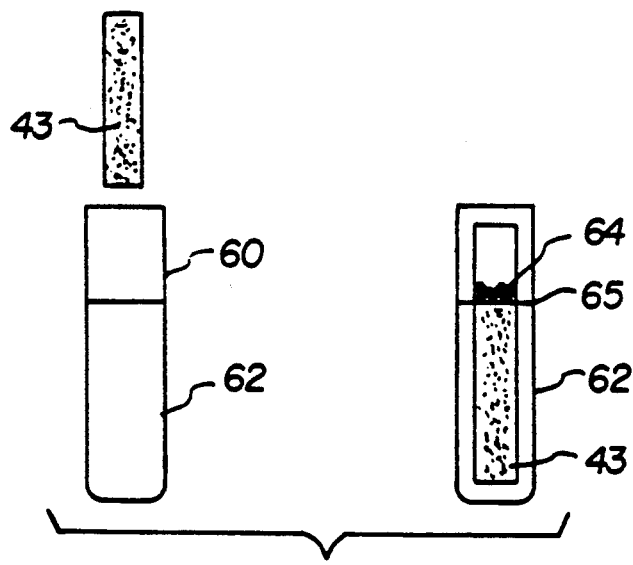
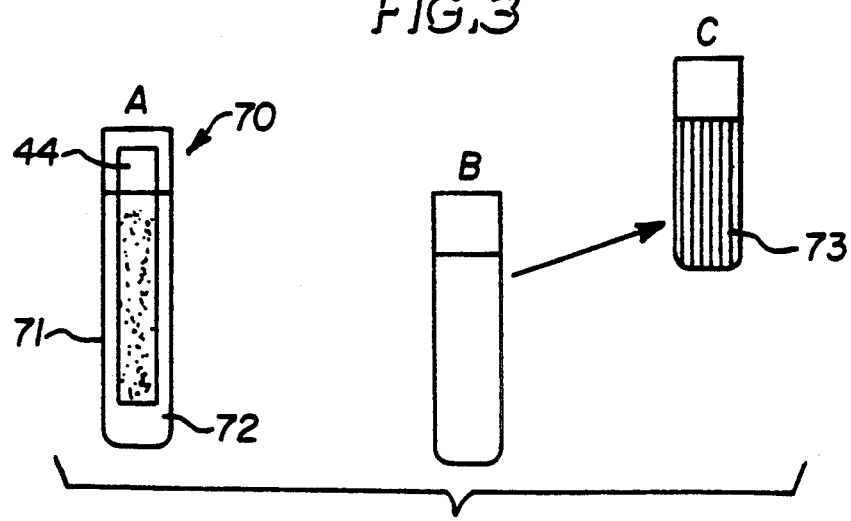

METHOD AND APPARATUS FOR TESTING MAI (MYCOBACTERIUM AVIUM-INTRACELLULARE) FOR ANTIMICROBIAL AGENT SENSITIVITY

CROSS-REFERENCE TO RELATED APPLICATION

This application is a continuation-in-part of U.S. patent application Ser. No. 07/426,573 filed Oct. 24, 1989 now U.S. Pat. No. 5,153,119.

BACKGROUND OF THE INVENTION 1. Field Of The Invention:

This invention relates to a method and apparatus for testing *Mycobacteria avium-intracellulare* ("MAI") for antimicrobial agent sensitivity. 2. Description Of The Prior Art:

Human immunodeficiency virus type 1 or HIV causes acquired immunodeficiency syndrome ("AIDS") which is a fatal disease approaching epidemic proportions throughout the world. By current estimates, about 15-34% of infected individuals will probably develop AIDS within 3-5 years. During the asymptomatic stage of AIDS, although most patients have no symptoms, some patients a few weeks after exposure develop a disorder resembling mononucleosis. Later, its symptoms include fatigue, fever and swollen glands, diarrhea and minor infections. Most of these symptoms disappear initially, but may recur. When AIDS develops, it is usually characterized by a major opportunistic infection, such as Pneumocystis pneumonia, or an opportunistic tumor, such as Kaposi's sarcoma or a lymphoma. At this stage, the disease is uniformly fatal.

It has been found that more than 50% of the AIDS patients have MAI present in their bodies. Wallace, J. M. and Hannah, J. B., "*Mycobacterium avium* Complex in Patients with Acquired Immunodeficiency Syndrome-A Clinicopathologic Study", *Chest* 93(5): 926-932 (1988). The MAI complex infection in AIDS patients has been shown to be widely disseminated in the patient, however the most common source of isolation is in the blood. There is currently no effective treatment against MAI as these organisms are often resistant to standard therapy.

It is known to use isolation techniques for determining the presence or absence of MAI in the patient's blood. One method involves using the BACTEC Radiometric System, which is a product of the Johnston Division of Becton and Dickenson. The system itself utilizes hemoculture tubes that contain Middlebrook 7H12 liquid broth plus 0.05% (v/v) sodium polyanethyl sulphonate in hemoculture vials. In addition, the 7H12 broth contains Carbon-14 labeled palmitic acid. In use, vials containing mycobacterial growth give off Carbon-14 labeled $CO_2$ and this is detected by a device similar to that used for liquid scintillation counter capable of detecting beta emitters. See Kirihara, J. M. et al. "Improved Detection Times for *Mycobacterium avium* Complex and *Mycobacterium tuberculosis* with BACTEC Radiometric System", *J. Clin. Microbiol.* 22:841-845 (1985).

Another method of isolation involves using genetic probes which rely upon DNA hybridization. Gonzalez, R. et. al., "Evaluation of Gen-Probe DNA Hybridization Systems for the Identification of *Mycobacterium tuberculosis* and *Mycobacterium avium-intracellulare* Diagnosis", *Microbiology Infect. Dis.* 8:69-77 (1987).

These known methods, although effective, require expensive equipment and specialized operating personnel and materials. Thus, smaller hospital centers where few AIDS patients are seen, field laboratories, and third world countries, where resources are limited, do not have this specialized equipment and personnel. A simpler and more inexpensive method and apparatus of isolating and identifying MAI would be of substantial benefit in such situations.

It is known that many *atypical Mycobacteria* grow on basal salt media devoid of any carbon sources other than paraffin wax which is introduced into the media in the form of paraffin wax coated rods. Fuhs, G. W., "Der Mikrobielle Abbau Von Kohlenwasserstoffen", *Arch. Mikrobiol.* 39:374-422 (1961). Mishra, S. K. et al., "Observations On Paraffin Baiting As a Laboratory Diagnostic Procedure in Nocardiosis", *Mycopathologica and Mycologia Applicata* 51 (2-3):147-157 (1973) utilized paraffin coated rods and basal salt medium to isolate *Nocardia asteroides* from clinical specimens such as sputum, bronchial lavage and cerebrospinal fluid.

The technique was further improved by substituting paraffin wax coated slides for rods and thereby making possible the use on an in situ Kinyoun cold acid-fastness staining procedure for organisms growing on the paraffin coated slide. Ollar, R. A., "A Paraffin Baiting Technique that Enables a Direct Microscopic View of "in situ" Morphology of *Nocardia asteroides* with the Acid-Fast or Fluorescence Staining Procedures", *Zbl. Bakt. Hyg., Abt. Orig. A*, 234:81-90 (1976). With this assay, a positive reaction tells the user immediately that a mycobacteria organism other than *M. tuberculosis* is present.

Once MAI is identified, there remains a need to test the MAI for antibiotic sensitivity. U.S. Pat. No. 3,826,717 provides an antibiotic sensitivity test container which includes a plurality of wells which contain a solid nutrient media. The wells are positioned in rows with each row containing a single antibiotic and different wells within the row having different concentrations. A control well is provided which contains no antibiotic but the media.

Despite the above teachings, however, there still remains a need for efficient and economical method and an inexpensive apparatus for testing MAI for antimicrobial agent sensitivity.

SUMMARY OF THE INVENTION

The present invention has met the above-described needs by providing an apparatus and method for determining the sensitivity of MAI to different antimicrobial agents and dosages. The apparatus comprises a plurality of test tubes each adapted to contain an amount of antimicrobial agents to be tested and MAI complex organisms to be assayed and a plurality of paraffin coated slides adapted for placement in each of the test tubes. Observing growth of the MAI complex organisms on the slides can be used to determine the concentration of the antimicrobial agents necessary to resist the MAI complex organism growth on the slide. The method comprises providing a plurality of test tubes each containing an amount of antimicrobial agents to be tested and MAI complex organisms to be assayed, incubating the test tubes and observing the MAI complex organism growth on the slides at discrete time intervals. In this way, the minimum inhibitory concentration ("MIC") of the antimicrobial agents necessary to resist the MAI complex organism growth on the slide can be determined.

It is an object of the invention to identify and speciate MAI by a method that is simple and efficient.

It is a further object of the invention to provide an MAI identification apparatus that is inexpensive and easy to use.

It is a further object of the invention to provide an MAI identification apparatus that does not require specialized training for a person to operate.

It is a further object of the invention to provide for a plurality of different tests to determine the presence or absence of MAI in a specimen.

It is a further object of the invention to provide a method that reduces the risk of contamination.

It is a further object of the invention to provide a method and apparatus for testing the sensitivity of antimicrobial agents to the MAI organism.

These and other objects will be more fully understood with reference to the description and to the drawings appended to this application.

BRIEF DESCRIPTION OF THE DRAWINGS

FIG. 1 shows a schematic front elevational view of a test tube holding the paraffin coated slide in a sterile aqueous solution inoculated with MAI.

FIG. 2 shows a schematic view of the acid-alcohol fastness assay.

FIG. 3 shows the tellurite reduction assay.

FIG. 4 shows the nitrate reduction assay.

DESCRIPTION OF THE PREFERRED EMBODIMENTS

Figure 5:
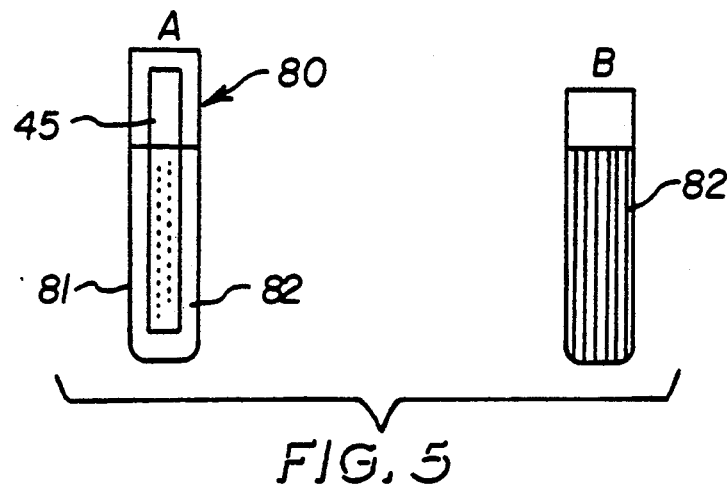
FIG. 5 shows the urea hydrolysis assay.

When referred to herein, the term "atypical Mycobacteria" means all mycobacteria other than *M. tuberculosis, M. leprae*, and *M. paratuberculosis*.

Referring to FIG. 1, part of the MAI isolation and speciation kit 10 is shown. FIG. 1 shows a standard test tube 12 which contains a sterile aqueous solution 14 (such as Czapek broth) and a cotton plug 16 to seal the tube 12. In use, the specimen to be tested for the presence or absence of MAI is introduced into the test tube 12 and the paraffin coated slide 18 is subsequently analyzed. The specimen can be an amount of a patient's blood, stool or sputum. The latter two specimens can be directly inoculated into the MAI isolation and speciation kit without the need for some sort of hemoculture broth.

Preferably, the slides 18 are prepared by first cutting standard microscope slides longitudinally so that they fit into the test tubes 12 and so they can be easily withdrawn. The test tubes 12 are plugged and sterilized by autoclaving.

The paraffin coating on the slides is preferably accomplished by first melting several tubes of sterilized histological grade paraffin embedding wax in a boiling water bath, while separately, a glass petri dish containing a slide support is heated on an electric hot plate to a temperature sufficient to keep the paraffin molten. The molten paraffin wax is then poured into the heated petri dish to a level sufficient to cover a slide on the support.

Ethanol-flame sterilized forceps are preferably used to transfer a previously uncoated slide onto the slide support in the heated petri dish which contains the molten wax. The slide is immersed in the molten wax for a few seconds such that it is covered by a thin coat of paraffin wax. A plurality of slides are prepared in this same fashion, with a tube of molten paraffin wax added after 6-10 slides have been prepared to ensure that there is always sufficient wax to cover the supported slides.

The Czapek broth 14 can be provided with an antibacterial and antifungal/antibiotic cocktail such as that sold under the trade name "PANTA" made by Becton Dickenson/Johnston Labs Division. This product will resist possible contaminating factors such as *Pseudomonas aeruginosa* or *Candida tropicalis*. This product has no effect on the MAI since the MAI is resistant to the currently used antibiotics in "PANTA".

The kit 10 can also serve as a means of distinguishing between *atypical Mycobacteria* and nocardioform organisms on the one hand and *Mycobacterium tuberculosis* on the other hand because the latter cannot utilize paraffin wax as a sole source of carbon. As is known, a tropism is created between the paraffin and organisms capable of using the paraffin as its carbon source, such as *atypical Mycobacteria* and nocardioform organisms. The outward manifestation of this tropism or baiting is the appearance of growth on the paraffin surface.

Once it is determined that a Mycobacteria other than *Mycobacteria tuberculosis* or a nocardioform organism is present on the slide, an alcohol-acid fastness test 40 (FIG. 2) can be used to further distinguish between the *atypical Mycobacteria* and the nocardioform organisms. As is known, *atypical Mycobacteria* are alcohol-acid fast; nocardioform organisms are acid-fast and *Pseudomonas aeruginosa* or *Candida tropicalis* are neither acid nor alcohol-acid fast. Thus, these latter two groups (nocardioforms and *Pseudomonas aeruginosa* or *Candida tropicalis*) can be eliminated as possibilities by the alcohol-acid fastness testing kit 40.

Referring to FIG. 2, the acid-alcohol fastness testing means 40 is shown. This testing means 40 includes a plurality of test tubes containing different solutions. The solutions stain the MAI on the slide for subsequent analysis under a microscope.

The paraffin coated slide culture with visible MAI growth 42 is removed from the test tube 12 of FIG. 1 and is first immersed in two consecutive tubes of distilled water 50, 51 and then immersed in a tube of Kinyoun carbolfuchsin 52 for fifteen minutes. The slide 42 is again immersed in a tube of distilled water 53 and then placed in a tube 54 containing acid-alcohol consisting of 97 ml absolute ethanol and 3.0 ml concentrated HCl for five minutes. After this, the slide is washed in a fourth tube of distilled water 55 and then placed into a tube 56 of 1.0% (v/v) aqueous Methylene blue solution for 1 minute. Finally, the slide is washed in a fifth tube 57 of distilled water.

The slide culture is then removed from the fifth tube 57 of distilled water and blotted gently with a clean absorbent paper tissue. The slide culture is then viewed under a microscope at 250x, 450x and 1000x oil immersion.

FIG. 3 shows the tellurite reduction assay which consists of a test tube 60 filled, preferably, with a Czapek broth plus an amount of potassium tellurite reagent 62. A cultured slide 43 is immersed into the test tube 60 and incubated. If MAI is present on the slide, a heavy black precipitate 64 forms at the level of the meniscus pellicle 65 of the slide 43. This test alerts the user to the possibility of MAI presence. MAI presence can be confirmed after the assay results are known for the assays discussed hereinafter.

FIG. 4 shows the nitrate reduction assay 70. A slide culture 44 showing heavy growth is assayed for the ability to reduce nitrates to nitrites. This is done by adding nitrates to a tube 71 containing a sterile broth. After a period of 12-24 hours incubation at 37° C., the slide 44 is removed from the sterile nitrate broth 72 and five drops of sulfanilic acid reagent solution followed by five drops of alpha naphthylamine reagent solution are added to the tubes 71. The reduction of nitrate to nitrite appears as a red colored broth 73. As is known, if the nitrate is reduced to nitrite, this indicates the absence of MAI on the slide.

FIG. 5 shows the urea hydrolysis reaction assay 80. A slide culture 45 is added to a plugged tube 81 containing 4.5 ml of sterile urea broth 82. The culture is incubated at 37° C. and checked after a period of three days. A positive reaction involves a color change of the broth 82 to pink or red after a period of three days. As is known, if the solution changes color, this indicates the absence of MAI on the slide 45.

Figure 6:
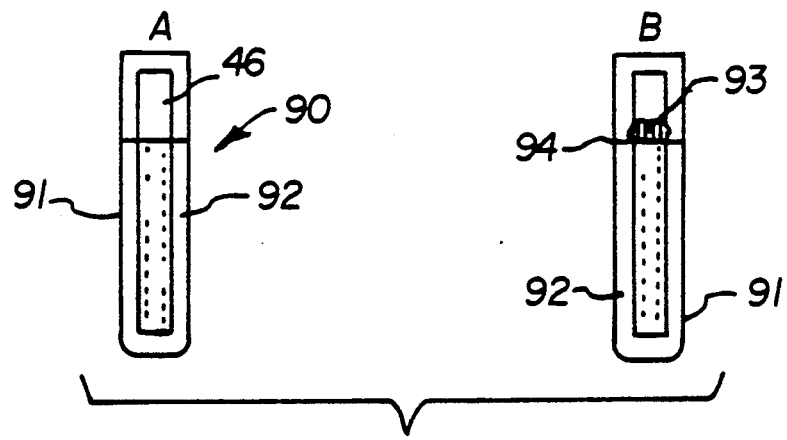
FIG. 6 shows the Tween 80 hydrolysis assay.

FIG. 6 shows the emulsifier hydrolysis assay 90. The emulsifier used is "Tween 80", a trademark of Atlas Chemical Industries, Inc. and is generically described as polyoxyethylene derivatives of fatty acid partial esters of sorbitol anhydrides. A slide culture 46 was added to sterile plugged tubes 91 containing Tween 80 media 92 and incubated at 37° C. A positive reaction involved the appearance of a red coloration 93 on the meniscus pellicle 94 of the slide 46 within five days. As is known, the presence of the red coloration in the slide indicates the absence of MAI on the slide.

It will be appreciated that at least one of the MAI identification tests (tellurite reduction, nitrate reduction, urea hydrolysis or "Tween 80" hydrolysis) should be performed, with the tellurite reduction test being the most important of the four tests. Preferably, all four of the tests should be performed in order to more accurately speciate and identify MAI.

Figure 7:
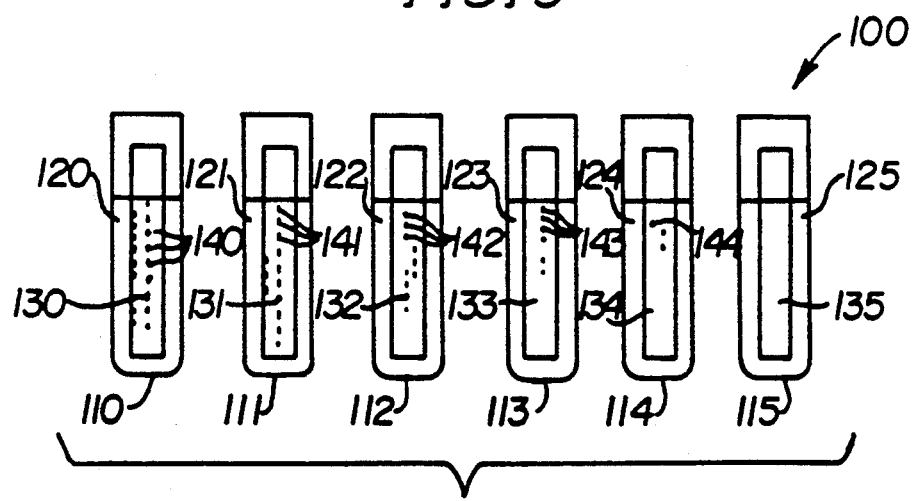
FIG. 7 shows the antimicrobial agent sensitivity testing assay of the invention.

FIG. 7 shows the antimicrobial agent sensitivity testing assay 100 of the invention. This method and the associated apparatus tests the sensitivity of the MAI to different antimicrobial agent and/or dosages of antimicrobial agent. The assay consists of preferably six tubes 110-115 each containing an amount of Czapek broth solution 120-125 and an amount of a specimen containing MAI to be tested. Broth solutions 121-125 contain uniform intervals of increasing concentration of an antimicrobial agent to be tested. Broth 120 does not contain an amount of the antimicrobial agent as this tube 110 will be the "control" tube. Tube 110, preferably, contains an amount of saline.

Paraffin slide cultures 130-135 were prepared as was discussed hereinbefore. Each of these slide cultures 130-135 are introduced into their respective tubes 110-115. The tubes 110-115 with slide cultures 130-135 are then incubated at 37° C. and checked at six days, seven days, eight days and ten days. By observing the MAI growth 140-144 on the paraffin surfaces of each of the slide cultures 130-135, the minimal inhibitory concentration (MIC) of antimicrobial agent necessary to prevent MAI growth on the paraffin culture slides 130-135 can be determined. In the case of FIG. 7, the MIC concentration is found in tube 115 because there is no MAI growth on slide 135.

EXPERIMENTAL RESULTS

A. Materials

1. Strains

Strains of MAI used in the following experiments were originally isolated from AIDS patients at St. Vincent's Hospital and Medical Center of New York and at Memorial Sloan-Kettering Cancer Center. The strains from both institutions were identified by routine morphologic and microbiological procedures with confirmation by DNA hybridization (Gene Probe Kit: Biogen) for *M. avium* and *M. intracellulare*. Strains isolated at St. Vincent's Hospital were 10,000; 1762; 1516; 15113; 8515; 6475; 5097; 8197; and 4861. Those from Memorial Sloan-Kettering Cancer Center were SK015; SK016; SK095; SK069; SK034; SK060; and SK024. All strains were isolated from patients with AIDS and identified as *M. avium* species with the exception of SK069 which was an *M. intracellulare* isolated from an immunocompetent patient with cavitary pulmonary disease.

2. Antimicrobial Agents

Stock solutions of chemotherapeutic agents were prepared. Amikacin (Bristol-Myers) was dissolved in distilled water and filter-sterilized; azithromycin (Pfizer) was dissolved in 95% ethanol and filter sterilized; and ciprofloxacin (Miles Laboratories) was dissolved in distilled water and filter-sterilized.

B. Paraffin Slide Culture Assay

A paraffin slide culture assay for antibiotic sensitivity in accordance with the method of the invention and done with apparatus described and shown in FIG. 7 was performed on the strains described above in connection with the antimicrobial agents also described above.

Standard microscope slides were longitudinally cut, sterilized, and coated with a thin layer of Paraplast compound (histological grade paraffin wax plus plastic polymers-Monoject Scientific Division of Sherwood Medical, St. Louis, Mo., 63103, USA). The best paraffin wax coatings were those that were extremely thin. This was achieved by quickly dipping the slide into molten paraffin wax and rapidly removing it from same. When a paraffin wax coating was too thick, the wax layer often sloughed off after prolonged incubation at 37° C. After the coating process, the slides were stored in sterile cotton-plugged tubes until needed.

1. Ciprofloxacin - HCL

Using the apparatus of FIG. 7, into each of the tubes 111-115 was introduced 0.5 ml of infectious inoculum, the initial working antimicrobial solution, the paraffin coated slides 131-135 and 4.5 ml of Czapek broth. A control tube 110 contained 0.5 ml of infectious inoculum, 0.5 ml of normal saline and 4.5 ml of Czapek broth. The control tube 110 also contained a paraffin coated slide 130. Each tube 111-115 contained increasing antimicrobial agent concentrations with tube 111 containing 3.6 micrograms/ml; tube 112 containing 7.3 micrograms/ml; tube 113 containing 10.9 micrograms/ml; tube 114 containing 14.5 micrograms/ml; tube 115 containing 18.2 micrograms/ml.

The experiments were done for each of the strains to make up one series of experiments. The same experiments were repeated for a second series. The paraffin control slide cultures in each of the experiments were usually read after 5-10 days incubation of 37° C., with 8 days being the preferred waiting period.

Table One lists the strains and reports the MIC and days of confluency for each strain for each experiment series. The MIC is defined as the lowest concentration of antimicrobial agent necessary to inhibit growth on the slides. The MIC is measured in units of micrograms/ml.

TABLE ONE

| Strains | Exp. Series I | | Exp. Series II | |
|---|---|---|---|---|
| | MIC | Days to confluency | MIC | Days to confluency |
| 10.000 | 3.6 | 9 | 3.6 | 7 |
| 1762 | 18.2 | 9 | 14.5 | 8 |
| 1516 | NG* | NG | 3.6 | 8 |
| 15113 | 3.6 | 10 | 3.6 | 9 |
| 8515 | 7.3 | 9 | 7.3 | 8 |
| 6475 | 3.6 | 10 | 7.3 | 9 |
| 5097 | 3.6 | 10 | 7.3 | 8 |
| 8197 | 3.6 | 9 | 3.6 | 8 |
| 4861 | 3.6 | 10 | 3.6 | 8 |
| SK015 | 14.5 | 7 | 14.5 | 6 |
| SK016 | 7.3 | 7 | 7.3 | 6 |
| SK095 | 10.9 | 7 | 7.3 | 6 |
| SK069 | 18.2 | 8 | >18.2 | 7 |
| SK037 | 18.2 | 7 | 14.5 | 7 |
| SK060 | 7.3 | 7 | 7.3 | 7 |
| SK024 | 7.3 | 7 | 3.6 | 6 |

*NG = No Growth.

The basic methodology of the invention was derived from experimental Series I with ciprofloxacin-HCL. As expected, the control tube showed the greatest amount of growth on the paraffin wax surface. When visible confluent growth on the paraffin slide surface in the control tube occurred, the tubes 111-115 containing varying dilutions or ciprofloxacin were examined. The effects of increased concentration of ciprofloxacin-HCL on MAI growth were clearly visible on the paraffin slides. The concentration of ciprofloxacin in the tube containing the lowest antimicrobial concentration in which there were no visible colonies on the paraffin wax coated slide was defined as the minimal inhibitory concentration (MIC) for this system. Lack of growth at this concentration was confirmed by microscopic examination of slides stained by the Kinyoun acid-fast staining method. This method was used to determine the MIC in all subsequent series of the antimicrobial sensitivity tests.

There was no statistically significant variation of Series II and III for ciprofloxacin-HCL (normal approximation with continuity correction=0.419 two-tailed p value for normal approximation=0.68). This confirmed the reproducibility of the method between experimental series. The MIC values obtained in these experimental series were quite close to those obtained by other investigators. See, for example, Heifets, L. and Lindholm-Levy, P. "Comparison of bactericical activities of streptomycin, amikacin, kanamycin and capreomycin against *Mycobacterium avium* and *M. tuberculosis*", *Antimicrob. Ag. Chemother*, 1989:33:1298-1301.

2. Azithromycin Testing

Again using the apparatus of FIG. 7, into each of the tubes 111-115 was introduced 0.5 ml of infectious inoculum, the initial working antimicrobial solution, the paraffin coated slides 131-135 and 4.5 ml of Czapek broth medium. A control tube 110 of azithromycin contained 0.5 ml of 95% ethanol in 4.5 ml Czapek broth and 0.5 ml of infectious inoculum along with slide 130. Each tube 111-115 contained increasing antimicrobial agent concentrations with tube 111 containing 2.6 micrograms/ml; tube 112 containing 5.3 micrograms/ml; tube 113 containing 7.9 micrograms/ml; tube 114 containing 10.6 micrograms/ml; tube 114 containing 10.6 micrograms/ml; tube 115 containing 13.2 micrograms/ml.

The experiments were done for each of the strains to make up one series of experiments. The same experiments were repeated for a second series and were repeated again for a third series. The paraffin coated slide culture in each of the experiments were usually read after 5-10 days incubation at 37° C., with 8 days being the preferred waiting period.

Table Two lists the strains and reports the MIC (in micrograms/ml) and days at confluency for each strain for each of the experimental Series I, II and III.

TABLE TWO

| | EXP. SERIES I | | EXP. SERIES II | | EXP. SERIES III | |
|---|---|---|---|---|---|---|
| Strains | MIC | Days to Confluency | MIC | Days to Confluency | MIC | Days to Confluency |
| 10.000 | 2.6 | 6 | 2.6 | 6 | 2.6 | 6 |
| 1762 | 5.3 | 7 | 2.6 | 6 | 5.3 | 6 |
| 1516 | 2.6 | 8 | 2.6 | 8 | 5.3 | 8 |
| 15113 | 5.3 | 8 | 5.3 | 10 | 2.6 | 6 |
| 8515 | 5.3 | 8 | 2.6 | 6 | 2.6 | 6 |
| 6475 | 2.6 | 8 | 2.6 | 8 | 2.6 | 6 |
| 5097 | 7.9 | 6 | 2.6 | 6 | 5.3 | 6 |
| 8197 | 5.3 | 7 | 2.6 | 6 | 2.6 | 6 |
| 4861 | 5.3 | 10 | 2.6 | 6 | 2.6 | 6 |
| SK015 | 7.9 | 7 | 5.3 | 6 | 5.3 | 7 |
| SK016 | 7.9 | 10 | 10.6 | 6 | 5.3 | 8 |
| SK095 | 2.6 | 7 | 5.3 | 6 | 5.3 | 7 |
| SK069 | 2.6 | 7 | 2.6 | 6 | 5.3 | 8 |
| SK037 | 5.3 | 7 | 7.9 | 6 | 5.3 | 8 |
| SK060 | 2.6 | 7 | 7.9 | 6 | 2.6 | 6 |
| SK024 | 5.3 | 7 | 7.9 | 6 | 2.2 | 7 |

There was no significant variation between experimental series (Friedman Statistic corrected for ties=20.95, p=0.14, sample size=3, df=15).

The values obtained for the MIC for azithromycin were different from values obtained by other researchers. See, e.g., Inderlied, C. B., Kolonoski, P. T., Wu, M. and Young, L. S., "In vitro and in vivo activity of azithromycin (CP 62.993) against the *Mycobacterium avium* complex", *J. Infect. Dis.*, 1989:159:994-997. One explanation for this is that azithromycin is very sensitive to pH changes. The above experiments were performed at pH=7.5. At lower pH the azithromycin, which is a macrolide antibiotic, is completely ionized and therefore would have great difficulty in crossing the cytoplasmic membrane. This translates into the need for higher concentrations of azithromycin, thus leading to higher MIC values. Furthermore, there is no accepted standard for antimicrobial sensitivity of MAI to azithromycin.

3. Amikacin Testing

Using the apparatus of FIG. 7, into each tube 110-115 was introduced 0.5 ml of infectious inoculum, the initial working antimicrobial solution, the paraffin coated slides 131-135 and 4.5 ml of Czapek broth medium. Tube 110 is a control tube and did not contain any amikacin but instead contained 0.5 ml of 95% ethanol in 4.5 ml of Czapek broth and 0.5 ml of infectious inoculum along with slide 130. Each tube 111-115 contained increasing amikacin antimicrobial agent concentrations, with tube 111 containing 3.2 micrograms/ml; tube 112 containing 6.4 micrograms/ml; tube 113 containing 9.6 micrograms/ml; tube 114 containing 12.8 micrograms/ml; and tube 115 containing 16 micrograms/ml.

The experiments were done for each of the strains to make one series of experiments. The same experiments were reported for a second series and were repeated again for a third series. The paraffin slide cultures in each of the experiments were usually read after 5-10 days incubation at 37° C., with 8 days being the preferred waiting period.

Table Three lists the strains and reports the MIC and days of confluency for each stain for each.

TABLE THREE

| Strains | EXP. SERIES I | | EXP. SERIES II | | EXP. SERIES III | |
|---|---|---|---|---|---|---|
| | MIC | Days to Confluency | MIC | Days to Confluency | MIC | Days to Confluency |
| 10.000 | >16.0 | 7 | >16.0 | 7 | 3.2 | 5 |
| 1762 | >16 0 | 7 | 12.0 | 7 | 3.2 | 5 |
| 1516 | 6.4 | 8 | 6.4 | 9 | 6.4 | 12 |
| 15113 | 3.2 | 8 | 6.4 | 5 | 3.2 | 6 |
| 8515 | 6.4 | 7 | 3.2 | 5 | 3.2 | 5 |
| 6475 | 12.0 | 7 | 3.2 | 5 | 3.2 | 5 |
| 5097 | NG* | NG | 6.4 | 5 | 6.4 | 5 |
| 8197 | >16.0 | 7 | >16.0 | 7 | 3.2 | 5 |
| 4861 | 12.0 | 8 | 3.2 | 6 | 3.2 | 7 |
| SK015 | 6.4 | 6 | 6.4 | 6 | 3.2 | 5 |
| SK016 | 7.3 | 5 | 9.6 | 6 | 6.4 | 5 |
| SK095 | 3.2 | 5 | 6.4 | 6 | 6.4 | 5 |
| SK069 | 3.2 | 6 | 9.6 | 6 | 6.4 | 6 |
| SK037 | 9.6 | 5 | >16.0 | 6 | 6.4 | 5 |
| SK060 | 6.4 | 5 | 6.4 | 7 | 3.2 | 5 |
| SK024 | 6.4 | 5 | 9.6 | 6 | 3.2 | 5 |

*NG = No Growth.

There was no statistically significant variation of Series I, II and III (Friedman statistic corrected for ties=14.79, p=0.39 sample step=3, df=14). This confirmed the reproducibility of this test among series. The MIC values obtained in these experimental series were quite close to those obtained by other researchers. See, e.g., Inderlied, C. B., Young, LS. and Yamanda, J. K. "Determination of in vitro susceptibility of *Mycobacterium avium* complex isolates to antimycobacterial agents by various methods", *Antimicrob. Ag. Chemother,* 1987:32: 1697-1702.

It will be appreciated that the present invention provides a method and apparatus for testing MAI for antimicrobial agent sensitivity. The apparatus is easy to use and inexpensive and the method is accurate and efficient.

Whereas particular embodiments of the invention have been described hereinabove, for purposes of illustration, it will be evident to those skilled in the art that numerous variations of the details may be made without departing from the invention as defined in the appended claims.

What is claimed is:

1. A method of testing the sensitivity of MAI complex organisms to different antimicrobial agents and dosage concentrations thereof comprising:

providing a plurality of test tubes each containing an amount of an antimicrobial agent to be tested and MAI complex organisms to be assayed;

placing into each of said test tubes a separate paraffin coated slide;

incubating said test tubes; and observing said MAI complex organism growth on said slides at discrete time intervals, whereby the minimum inhibitory concentration of said antimicrobial agent necessary to resist said MAI complex organism growth on said slides can be determined.

2. The method of claim 1, including before placing said paraffin coated slides into said test tubes, introducing a sterile aqueous broth therein.

3. The method of claim 2, including providing one additional test tube as a control test tube containing an MAI complex organism to be assayed.

4. The method of claim 3, including incubating said test tubes at 37° C.

5. The method of claim 4, including observing said slides at 6 days, 7 days, 8 days, 9 days and 10 days after incubating said test tubes.

6. The method of claim 5, including introducing into said test tubes uniform intervals of increasing concentrations of said antimicrobial agent.

7. The method of claim 1, including employing as said antimicrobial agent one selected from the group consisting of amikacin, azithromycin and ciprofloxacin.

* * * * *